(12) United States Patent
McClintock

(10) Patent No.: US 10,869,707 B2
(45) Date of Patent: Dec. 22, 2020

(54) SURGICAL FIXATION ASSEMBLIES AND METHODS OF USING THE SAME

(71) Applicant: K2M, Inc., Leesburg, VA (US)

(72) Inventor: Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 19 days.

(21) Appl. No.: 15/999,654

(22) PCT Filed: Feb. 21, 2017

(86) PCT No.: PCT/US2017/018680
§ 371 (c)(1),
(2) Date: Aug. 20, 2018

(87) PCT Pub. No.: WO2017/143331
PCT Pub. Date: Aug. 24, 2017

(65) Prior Publication Data
US 2019/0254724 A1 Aug. 22, 2019

Related U.S. Application Data

(60) Provisional application No. 62/296,691, filed on Feb. 18, 2016.

(51) Int. Cl.
*A61B 17/86* (2006.01)
*A61B 17/70* (2006.01)
*A61F 2/46* (2006.01)

(52) U.S. Cl.
CPC ...... *A61B 17/8685* (2013.01); *A61B 17/7044* (2013.01); *A61B 17/8665* (2013.01); *A61B 17/8695* (2013.01); *A61B 17/7032* (2013.01); *A61F 2/4611* (2013.01)

(58) Field of Classification Search
CPC ............ A61B 17/8685; A61B 17/8695; A61B 17/8665; A61B 17/8615
See application file for complete search history.

(56) References Cited

U.S. PATENT DOCUMENTS

| | | | |
|---|---|---|---|
| 1,352,201 A | 9/1920 | Kennedy | |
| 4,295,760 A | 10/1981 | Warner | |
| 4,988,351 A * | 1/1991 | Paulos | A61B 17/8625 606/232 |
| 5,184,922 A * | 2/1993 | Blackwell | F16B 13/06 405/259.1 |
| 5,947,967 A * | 9/1999 | Barker | A61B 17/7037 606/278 |

(Continued)

OTHER PUBLICATIONS

International Search Report and Written Opinion issued in PCT/US17/18680 dated Jun. 19, 2017.

*Primary Examiner* — Ellen C Hammond
*Assistant Examiner* — Tara Rose E Carter
(74) *Attorney, Agent, or Firm* — Lerner, David, Littenberg, Krumholz & Mentlik, LLP

(57) ABSTRACT

A surgical fixation assembly includes a shank having an outer surface. The outer surface of the shank includes a threaded portion. The surgical fixation assembly includes a first cupped washer supported on the shank, a sleeve, and a nut threadably engaged with the threaded portion of the shank. The nut is positioned to slide the sleeve axially along the shank to deform the first cupped washer and enable the first cupped washer to penetrate osseous tissue for securing the shank to osseous tissue.

20 Claims, 7 Drawing Sheets

(56) References Cited

U.S. PATENT DOCUMENTS

| | | | |
|---|---|---|---|
| 5,967,724 A * | 10/1999 | Terry | F16B 31/028 |
| | | | 411/135 |
| 8,636,738 B2 | 1/2014 | McClintock et al. | |
| 8,834,539 B2 * | 9/2014 | Keren | A61B 17/8033 |
| | | | 411/371.2 |
| 2003/0009219 A1 * | 1/2003 | Seyr | A61F 2/0811 |
| | | | 623/13.14 |
| 2005/0273106 A1 * | 12/2005 | Oepen | A61B 17/866 |
| | | | 606/313 |
| 2008/0177330 A1 * | 7/2008 | Ralph | A61B 17/8038 |
| | | | 606/290 |
| 2014/0081343 A1 | 3/2014 | Deffenbaugh et al. | |
| 2014/0257412 A1 * | 9/2014 | Patty | A61B 17/8615 |
| | | | 606/308 |

* cited by examiner

SURGICAL FIXATION ASSEMBLIES AND METHODS OF USING THE SAME

CROSS REFERENCE TO RELATED APPLICATIONS

This application claims the benefit of U.S. Provisional Patent Application No. 62/296,691, filed Feb. 18, 2016, the entire disclosure of which is incorporated by reference herein.

TECHNICAL FIELD

The present disclosure relates generally to spinal surgery. More specifically, the present disclosure relates to surgical fixation assemblies for spinal stabilization and methods of use.

BACKGROUND

The human spine is the supporting axis of the body and makes all the movement of a person's head, arms, and legs possible. It is a highly flexible structure, capable of a high degree of curvature and twist in nearly every direction. An adult spine generally has twenty-four vertebrae, which can be categorized into three major sections. These categories include the cervical spine, the thoracic spine, and the lumbar spine. The cervical spine is composed of the upper seven vertebrae, the thoracic spine is composed of the next twelve vertebrae, and the lumbar spine is composed of the final five vertebrae. Below the lumbar spine is a bone called the sacrum, which is part of the pelvis. Muscles and ligaments are attached to a slender projection from the back of the vertebrae known as the spinous process. The spinal cord is housed within a narrow channel in the center of spine. All the nerves of the body are connected to the spinal cord.

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

Depending upon how such systems are coupled to the spine, the systems may be classified as anterior, posterior, or lateral implants. For example, lateral and anterior systems are coupled to the anterior portion of the spine. Posterior systems generally include a pair of rods that are fixed to adjacent vertebrae with fixation assemblies, such as pedicle screws on either side of the spinous process along a section of the spine. For example, several pedicle screws may be secured to a spine during a procedure and, depending upon the number of pedicle screws and the length of those pedicle screws, this process could be a very time and labor-intensive part of the procedure. In particular, each pedicle screw would require several rotations before becoming fully secured to the spine.

SUMMARY

Accordingly, one aspect of the present disclosure is directed to a surgical fixation assembly. The surgical fixation assembly may include a shank having an outer surface. The outer surface of the shank may include a threaded portion. The surgical fixation assembly may include a first cupped washer supported on the shank, a sleeve, and a nut threadably engaged with the threaded portion of the shank. The nut may be positioned to slide the sleeve axially along the shank to deform the first cupped washer and enable the first cupped washer to penetrate osseous tissue for securing the shank to osseous tissue.

In some embodiments, the surgical fixation assembly may include a second cupped washer. The first and second cupped washers may be supported axially adjacent to one another at spaced apart locations along the shank.

In certain embodiments, the surgical fixation assembly may include a first flat washer positioned between the first and second cupped washers to axially space the first and second cupped washers apart.

In embodiments, the surgical fixation assembly may include a second flat washer positioned adjacent the second cupped washer.

In some embodiments, the second cupped washer may be inverted and angularly displaced relative to the first cupped washer.

In certain embodiments, the sleeve may include a flange that extends radially outward from the sleeve and is positioned to limit an insertion depth of the shank.

In embodiments, the flange may include one or more spikes that extend distally therefrom.

In some embodiments, the flange may have an elliptical configuration.

In certain embodiments, the shank may include a conical tip positioned to provide a backstop for the first cupped washer to enable the first cupped washer to deform under a compression force applied thereto as the sleeve slides toward the conical tip.

In embodiments, the shank may have a cross-sectional shape configured to prevent the first cupped washer from rotating about the outer surface of the shank.

In certain embodiments, the first cupped washer may be configured to flatten as the sleeve moves distally along the shank.

According to another aspect of the present disclosure, a method for securing a shank to osseous tissue is provided. The method may include inserting a shank into a hole into osseous tissue, rotating a nut about the shank to drive a sleeve supported on the shank distally, and deforming a cupped washer supported on the shank as the sleeve slides along the shank to radially expand the cupped washer into osseous tissue for securing the shank to osseous tissue.

In embodiments, the method may include preventing the nut from moving in a proximal direction.

The method may include drilling the hole.

In some aspects, deforming the cupped washer may include flattening the cupped washer.

Other aspects, features, and advantages will be apparent from the description, the drawings, and the claims that follow.

BRIEF DESCRIPTION OF THE DRAWINGS

Various embodiments of the present disclosure are described herein below with reference to the drawings, wherein.

DETAILED DESCRIPTION

Figure 1A:
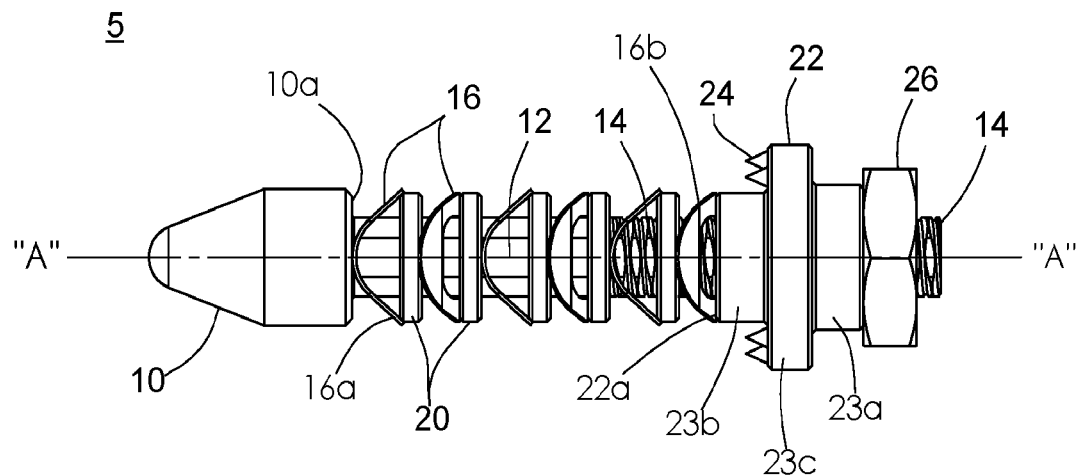
FIG. 1A is a side view of a fixation assembly in an undeployed position according to an embodiment of the present disclosure.

Various embodiments will now be described in detail with reference to the drawings, wherein like reference numerals identify similar or identical elements. As commonly known, the term "clinician" refers to a doctor, a nurse or any other care provider and may include support personnel. Additionally, the term "proximal" refers to the portion of structure that is closer to the clinician and the term "distal" refers to the portion of structure that is farther from the clinician. Further still, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

In general, the present disclosure relates to fixation systems including a fixation assembly for spinal stabilization. The fixation assembly is securable to osseous tissue, for example, the pedicle of a vertebra, the iliac of the pelvis, or the like. The fixation assembly described herein reduces the time and effort required for insertion into osseous tissue.

Figure 1B:
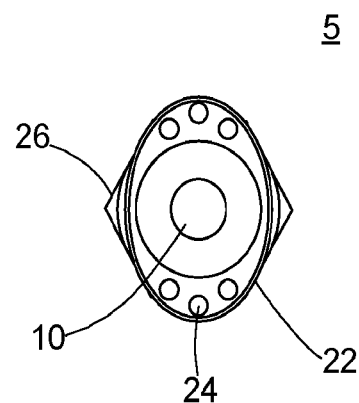
FIG. 1B is an end view of the fixation assembly of FIG. 1A.

Referring initially to FIGS. 1A and 1B, a fixation assembly 5 defines a longitudinal axis "A-A" and includes a shank 12 having a tip 10 that extends distally from shank 12. Shank 12 supports a fixation washer 16, a spacing washer 20, a sleeve 22, and a drive member 26.

Shank 12 of fixation assembly 5 defines a threaded portion 14 on an outer surface thereof. Threaded portion 14 is defined on the outer surface of shank 12 along a partial length of shank 12. In some embodiments, a full length of shank 12 may include threaded portion 14. Threaded portion 14 of shank 12 may include a locking thread (not shown) that prevents drive member 26 from backing out, or otherwise moving proximally, once drive member 26 advances distally past a respective one of wave segments 12a. Shank 12 may have any suitable circular or non-circular, transverse, cross-sectional shape such as square, rectangular, triangular, pentagonal, hexagonal, septagonal, octagonal, etc., or combinations thereof. In embodiments, shank 12 may include surface texturing, over-molding, coatings, ribbings, nubs, notches, grooves, etc., or combinations thereof to, for example, control (e.g., inhibit and/or facilitate) movement of washers 16, 20, sleeve 22, and/or drive member 22 along the outer surface of shank 12. For example, as seen in FIG. 2, shank 12 can include one or more ribs 12a at spaced apart locations about the outer surface of shank 12 that prevent washers 16, 20 from rotating about shank 12 while enabling one or more of washers 16, 20 to axially translate along the outer surface of shank 12.

With continued reference to FIG. 1A, tip 10 of shank 12 is configured for penetrating osseous tissue and may have any suitable size or shape for penetration of, and/or securement to, osseous tissue. Tip 10 may be integrally and/or monolithically formed with shank 12 and may have a conical configuration. Although shown as being blunt, tip 10 can have a sharpened configuration. A proximal end portion 10a of tip 10 has a diameter larger than a diameter of shank 12, as illustrated in FIGS. 1A and 2, for example, to prevent washers 16, 20 from falling off a distal end portion of shank 12 and to provide a backstop against which washers 16, 20 can be driven for effectuating a repositioning and/or deformation of washers 16.

Figure 2:
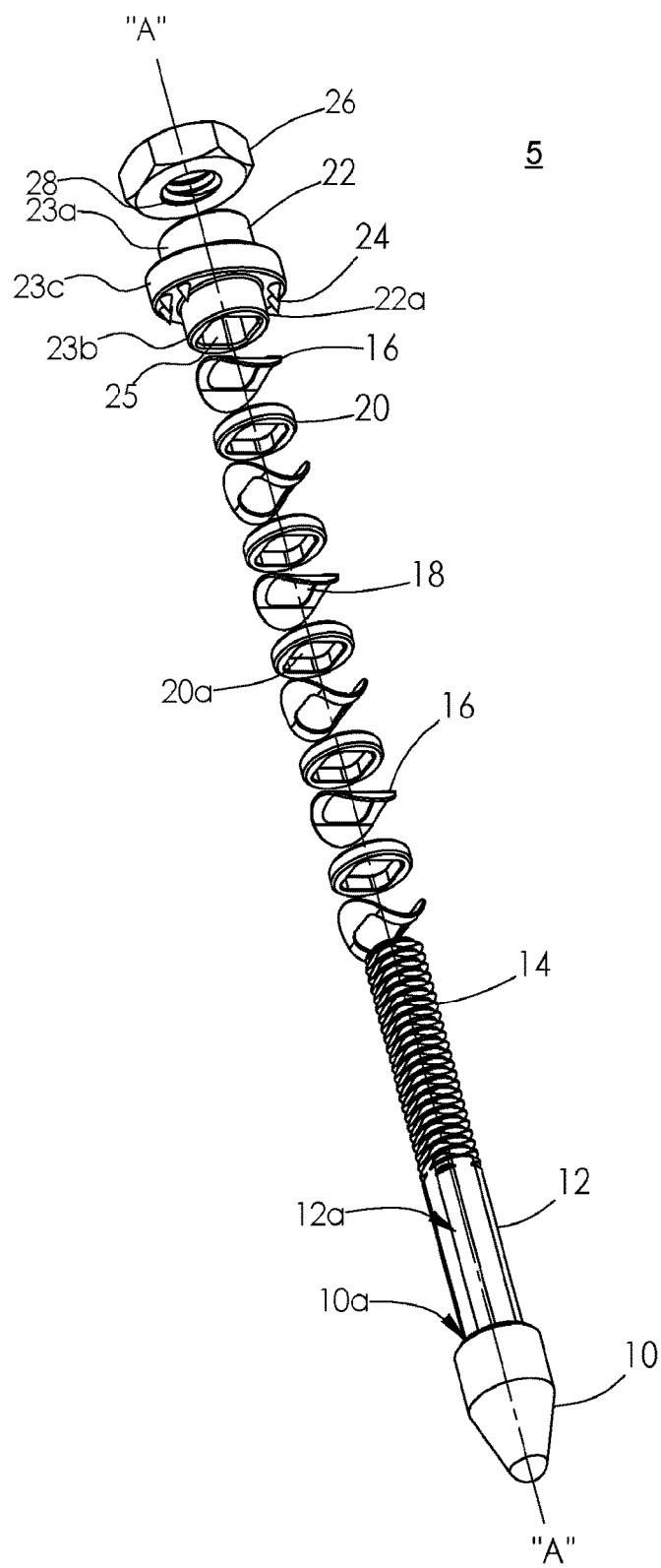
FIG. 2 is a perspective view, with parts separated, of the fixation assembly of FIG. 1A.

With reference to FIG. 2, washers 16, 20 of fixation assembly 5 are supported on shank 12. Washer 16 defines a bore 18 therethrough and washer 20 defines a bore 20a therethrough that is similar to bore 18 of washer 16. Bores 18 and 20a of washers 18, 20, respectively are configured to accommodate shank 12 such that washers, 16, 20 can be disposed along the outer surface of shank 12. Bores 18, 20a may have a shape configured to complement the outer surface of shank 12, or portions thereof, to prevent rotation of the washers 16, 20 about the outer surface of shank 12, or portions thereof. For example, bores 18, 20a may have a square or rectilinear shape to accommodate the transverse cross-sectional shape of shank 12 (FIG. 2), or portions thereof. Bores 18, 20a of washers 16, 20 may have any suitable circular or non-circular transverse cross-sectional shape that is the same, or different from, the transverse cross-sectional shape of shank 12, such as, for example, triangular, pentagonal, hexagonal, septagonal, octagonal, etc., or combinations thereof.

Figure 3:
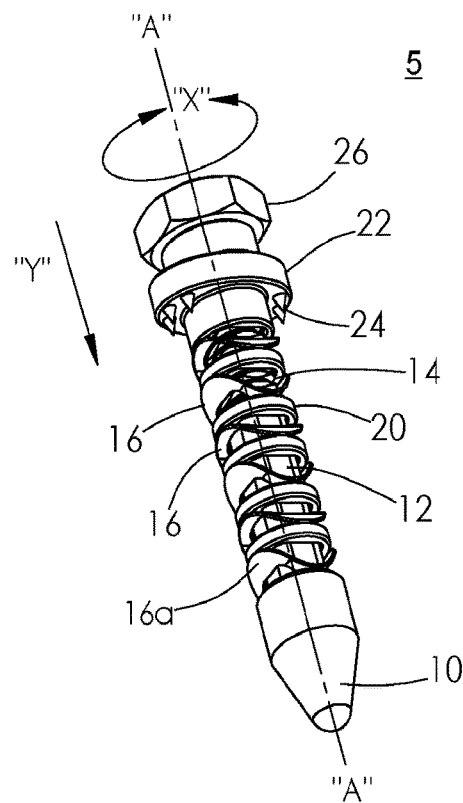
FIG. 3 is a perspective view of the fixation assembly of FIG. 1A.

As illustrated in FIGS. 1A, 2, and 3, washers 16 of fixation assembly 5 may be arched or cupped in an axial direction to define a concave and/or convex shape. Washers 16 may be cupped washers. Washers 16 are positioned to move or deform from an initial position, in which washers 16 are bent or cupped (FIGS. 1A-3), to a second position (FIGS. 4A-4C), in which washers 16 are unbent or flattened, upon application of axial force "FY" (FIG. 5A) in an axial direction "Y," to enable fixation assembly 5 to secure to osseous tissue. Washers 20 may have a flat cross-sectional shape and function to space washers 16 apart in both the first and second positions thereof.

Although washers 16, 20 can be positioned in any suitable arrangement relative to one another, washers 16 of fixation assembly 5 may be positioned along shank 12 and interspersed (e.g., in alternate arrangement with) with washers 20 to form a washer pattern (FIG. 2). For example, the pattern may be washer 16—washer 20—washer 16, etc. and can start and/or end with the same or different types of washer, e.g., washer 16 and/or washer 20. In one instance, as shown in FIGS. 1A and 3, a distal washer 16a is disposed at the distal end portion of the shank 12 that rests or abuts against proximal end portion 10a of tip 10 of shank 12 while a proximal washer 16b is in abutment with a distal end portion 22a of sleeve 22. Other washers 16 and 20 may be interleaved with one another between proximal and distal washers 16a, 16b such that each washer 20 abuts two different washers 16, one on each side thereof. Additionally or alternatively, longitudinally adjacent washers 16 can be inverted (e.g., mirrored relative to one another) and/or disposed at different angular positions relative to one another (e.g., 90 degrees out of phase) although any suitable angular displacement can be provided.

In some embodiments, two or more washers 16 can be positioned adjacent one another (e.g., contacting relation), for example, to increase tissue cutting at a longitudinal location of one or more of washers 16 along shank 12. In certain embodiments, two or more washers 20 can be positioned adjacent one another (e.g., contacting relation), for example, to increase spacing between a pair of washers 16.

In some embodiments, as seen in FIG. 3, a pattern of alternating washers 16, 20, in which each successive washer 16 is inverted and rotated relative to the preceding washer 16, may be provided along at least a portion of a length of shank 12, and in certain embodiments, along the entire length.

In embodiments, washers 16 and/or washers 20 may be formed from any suitable (e.g., biocompatible) material, such as plastic, nylon, ceramic, rubber, titanium, titanium alloy, stainless steel, nickel titanium, polyetheretherketone ("PEEK"), MP35N alloy (a non-magnetic, nickel, cobalt, chromium, molybdenum alloy), or the like. Additionally or alternatively, washers 16, 20 may be coated with a material (e.g., to enhance biocompatibility, corrosion resistance, or the like) using known processes, such as, for example, electroplating, metallizing, phosphating, browning, bluing, chemical plating, etc. In embodiments, the material used for forming washers 16, 20 may have a moderate to high elastic property so that washers 16 can be repositioned or deformed (e.g., flattened) for fixation into the osseous tissue and such that washers 16 may be returned to a pre-deformed (e.g., cupped) condition or position to remove fixation assembly 5 from osseous tissue. In certain embodiments, washers 16, 20 may be plain washers (e.g., Fender, penny, repair washers, etc.), spring or locking washers (e.g., Belleville, curved, wave, split, toothed, serrated, star, tab, etc.), and/or specialized washers (e.g., Keps nut, K-lock nut, top hat, shoulder, keyed, torque limiting, etc.).

With continued reference to FIGS. 1A, 2, and 3, drive member 26 of fixation assembly 5, which may be a nut, is initially disposed on a proximal portion of shank 12. Drive member 26 includes an internally threaded surface 28, which is configured to receive and/or engage threaded portion 14 of shank 12. Rotation (e.g., clockwise and/or counterclockwise) of drive member 26 about longitudinal axis "A-A" of fixation assembly 5, as indicated by arrows "X," causes drive member 26 to move axially (e.g., distally) along longitudinal axis "A-A," as indicated by arrow "Y," and along threaded portion 14 of shank 12 of fixation assembly 5.

Sleeve 22 of fixation assembly 5 is disposed distally of drive member 26 along the outer surface of shank 12 between drive member 26 and washers 16, 20. Although sleeve 22 and drive member 26 are shown as independent features, sleeve 22 and drive member 26 may be fixedly coupled together. Sleeve 22 includes a proximal body portion 23a, a distal body portion 23b, and a flange 23c disposed between body portions 23a, 23b that extends radially outward from sleeve 22. Body portions 23a, 23b of sleeve 22 are shown as being substantially cylindrical and flange 23c of sleeve 22 is shown as being elliptical (FIGS. 1B, 2, and 4A), but sleeve 22, or portions thereof, may have any suitable configuration. Sleeve 22 defines a central bore 25 therethrough that is configured to receive shank 12 and to enable sleeve 22 to slidably and axially (e.g., distally) move longitudinally along shank 12 of fixation assembly 5, as indicated by arrow "Y." Central bore 25 is configured to accommodate the cross-sectional shape of shank 12 to inhibit rotation of sleeve 22 about shank 12, similar to bores 18 and 20a of washers 16, 20, respectively.

Flange 23c of sleeve 22 is configured to abut osseous tissue to limit insertion depth of fixation assembly 5 when shank 12 is inserted, for example, into a drilled pilot hole in osseous tissue. Flange 23c includes one or more spikes 24 that extend distally from a distal surface of flange 23c to facilitate frictional engagement with osseous tissue surrounding the pilot hole to provide counter torque force while rotating drive member 26 relative to shank 12. In some embodiments, flange 23c may be devoid of spikes.

With reference to FIG. 3, in use, a hole (not shown) can be drilled or otherwise formed into osseous tissue using known devices and techniques (e.g., punching, cutting, coring, etc.). The hole may even be formed naturally. While in the initial position (see also FIG. 1A), the fixation assembly 5 can be inserted into the hole and advanced so that the spikes 24 of the sleeve 22 of the fixation assembly 5 are driven into osseous tissue surrounding the hole until the sleeve 22 abuts the osseous tissue (e.g., is fully inserted). Rotational force, as indicated by arrows "X," may be applied to drive member 26 to effectuate axial movement of drive member 26 along shank 12 in the direction "Y." Specifically, rotation of drive member 26 causes internally threaded surface 28 of drive member 26 to engage with threaded portion 14 of shank 12 so that drive member 26 advances sleeve 22 distally along shank 12 in direction "Y." As sleeve 22 moves distally along shank 12, sleeve 22 drives washers 16, 20 distally against proximal end portion 10a of tip 10, which causes washers 16, 20 to be compressed between sleeve 22 and tip 10.

Figures 4A, 4B:
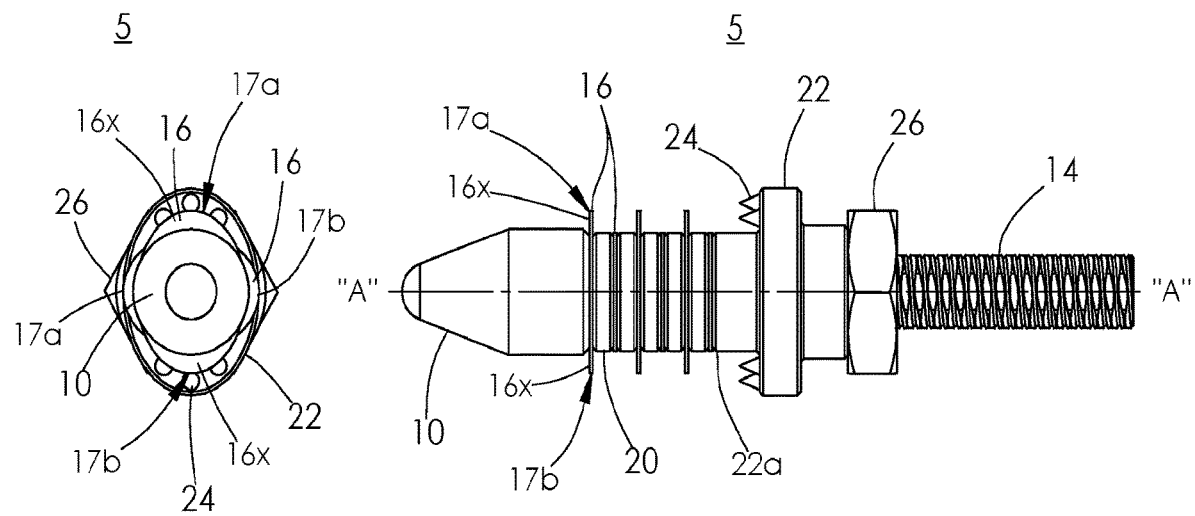
FIG. 4A is an end view of the fixation assembly of FIG. 1A in a deployed position.
FIG. 4B is side view of the fixation assembly of FIG. 1A in the deployed position.
Figure 4C:
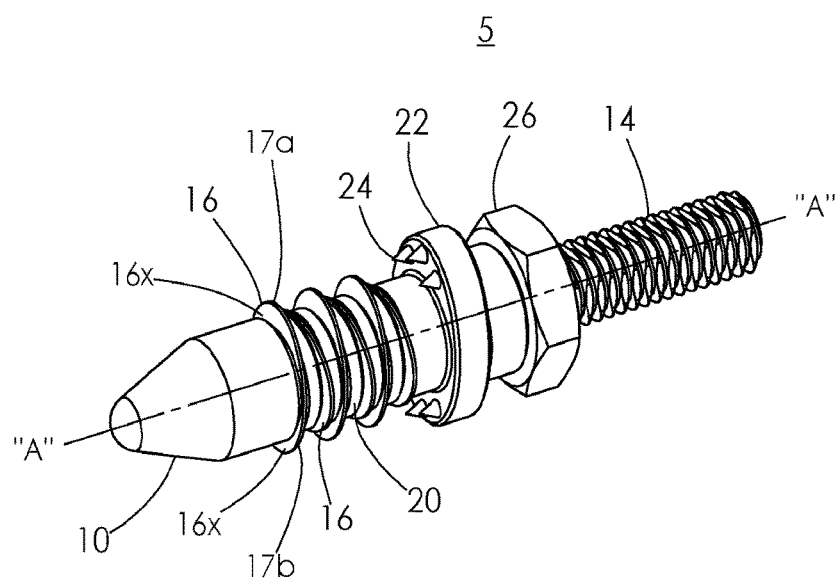
FIG. 4C is a perspective view of the fixation assembly of FIG. 1A in the deployed position.
Figure 5A:
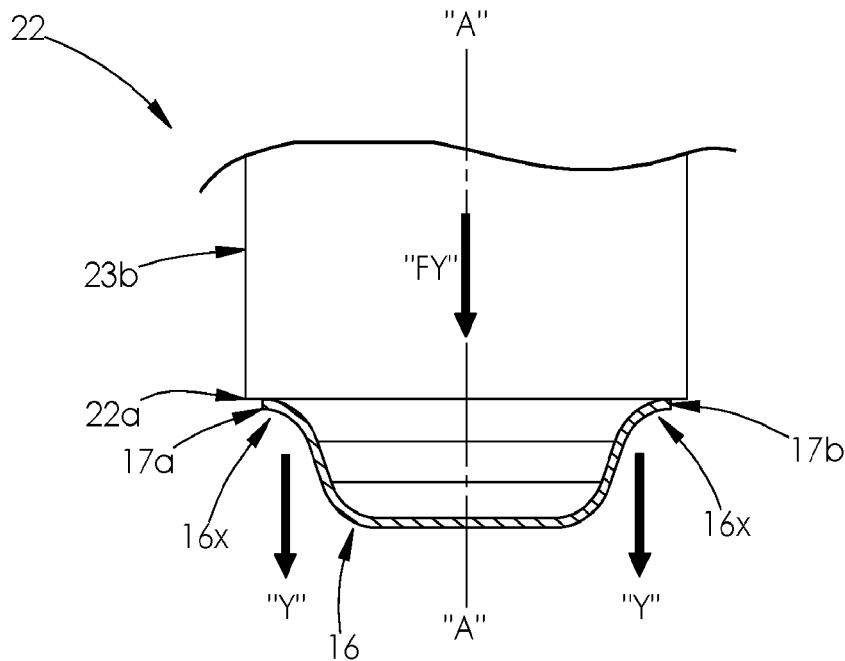
FIG. 5A is a side view of a sleeve of the fixation assembly of FIG. 1A shown exerting a force on a washer of the fixation assembly of FIG. 1A.
Figure 5B:
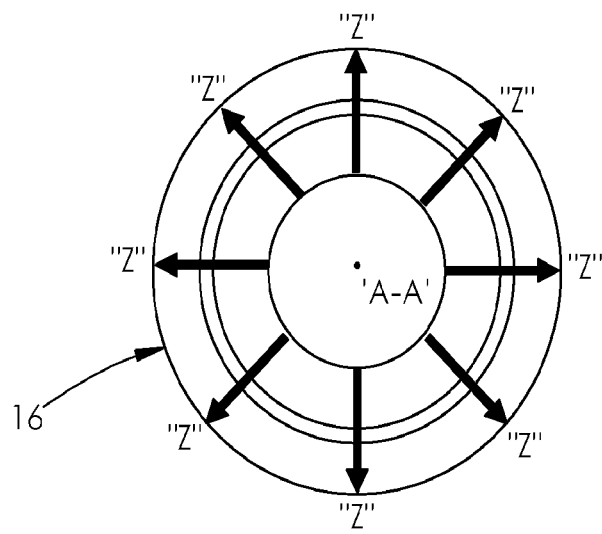
FIG. 5B is a top view of the washer of FIG. 5A.

With reference to FIGS. 5A and 5B, under application of the axial force "FY," washers 16 deform, expand, and/or flex radially outwardly, as indicated by arrows "Z" and downwardly or distally, as indicated by arrows "Y" so as to expand a diameter of washers 16 radially beyond a diameter of washers 20. Continued radial expansion of washers 16 deforms washers 16 into a second position (e.g., flattened or deformed), as shown in FIGS. 4A-C, so as to enable portions of an outer periphery 16x of washers 16 to extend beyond a diameter of washers 20. In particular, in a second position of washers 16, outer periphery 16x of washers 16 includes a first fin 17a and a second fin 17b that are disposed in mirrored relation on diametrically opposed ends of the respective washer 16, and positioned to cut into osseous tissue surrounding the pilot hole for securing fixation assembly 5 to the osseous tissue. Advantageously, securement of fixation assembly 5 is achieved with minimal time and rotational driving effort.

Referring back to FIGS. 4A-C, when washers 16 are in the second position (e.g., deformed), adjacent washers 16 are angularly displaced (e.g., 90 degrees relative to one another) to facilitate circumferential fixation about shank 12 of fixation assembly 5. Washers 16, while in the second position, (e.g., flattened), may have an elliptical shape.

The fixation assembly 5 may be shorter in length than a traditional bone screw and may be configured not to extend into predetermined portions of osseous tissue. For example, if the osseous tissue is a pedicle, then the fixation assembly 5 can have length that would not extend into the vertebral body interspace. Additionally, the fixation assembly 5, or portions thereof may be comprised of any biocompatible material. Non-limiting examples of such biocompatible material includes titanium, titanium alloy, stainless steel, nickel titanium, cobalt chrome, and polyetheretherketone ("PEEK").

Figure 6:
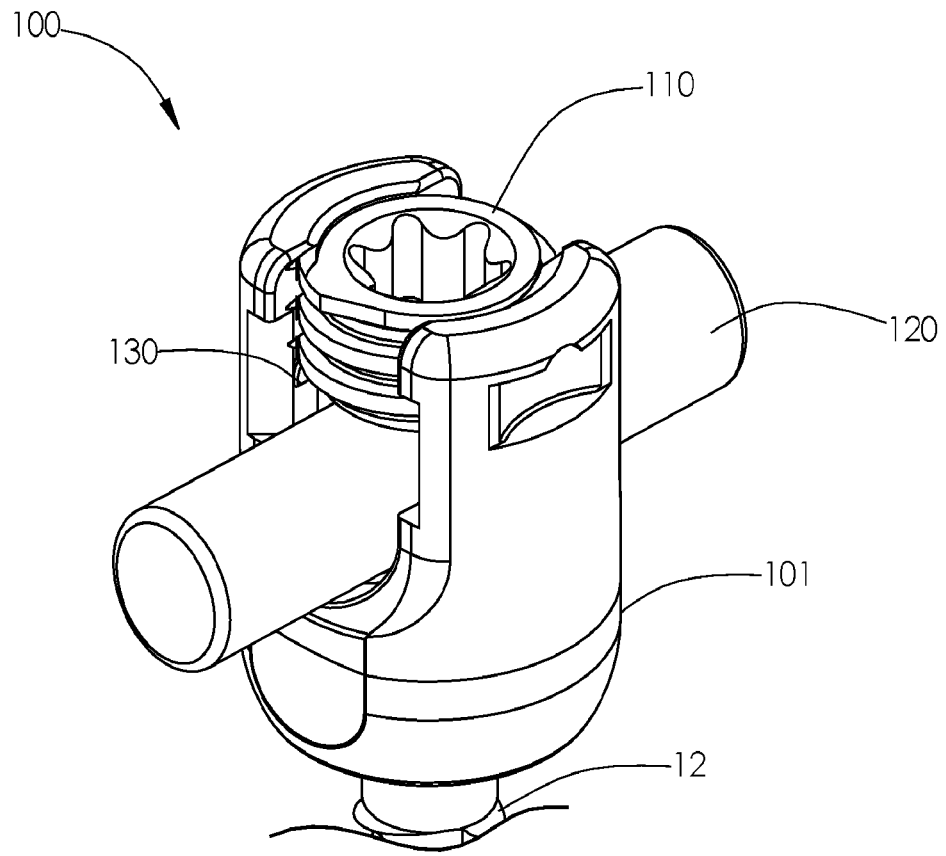
FIG. 6 is a perspective view of a fixation system according to another embodiment of the present disclosure.
Figure 7:
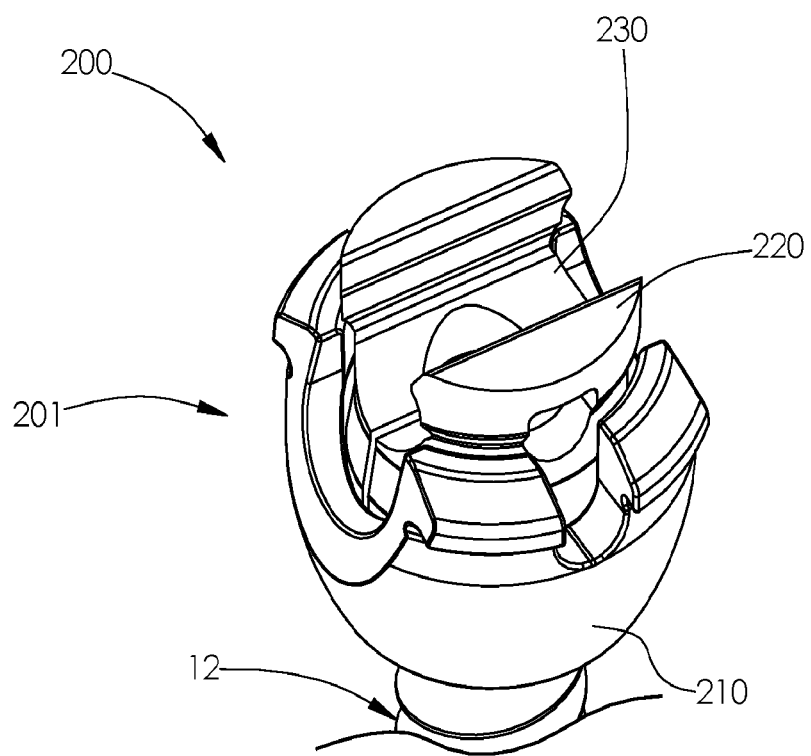
FIG. 7 is perspective view of a fixation system according to yet another embodiment of the present disclosure.

The presently disclosed fixation assemblies can be included as part of a fixation system. For example, threaded portion 14 of shank 12 can be coupled to a housing assembly for securing and stabilizing a spinal rod. In one instance, with reference to FIG. 6, a fixation system 100 is provided and includes a housing assembly 101, which can be provided as a set screw type arrangement in which a set screw 110 is threadably received within the housing assembly 101 to secure a spinal rod 120 within a U-shaped saddle 130 defined therein. Alternatively, with reference to FIG. 7, a fixation system 200 is provided. Fixation system 200 includes a housing assembly 201 that can be provided as a taper lock type arrangement in which an outer housing 210 is slidably movable (axially) relative to an inner collet 220 to selectively secure a spinal rod (not shown) within a U-shaped saddle 230 defined therein. Fixation systems 100 and 200 may include any or all parts of fixation assembly 5. For a more detailed description of such taper lock and/or set screw type housing assemblies, reference can be made to commonly owned U.S. Pat. Nos. 9,393,049 and 8,814,919, the entire disclosures of each of which are incorporated by reference herein.

Figure 8:
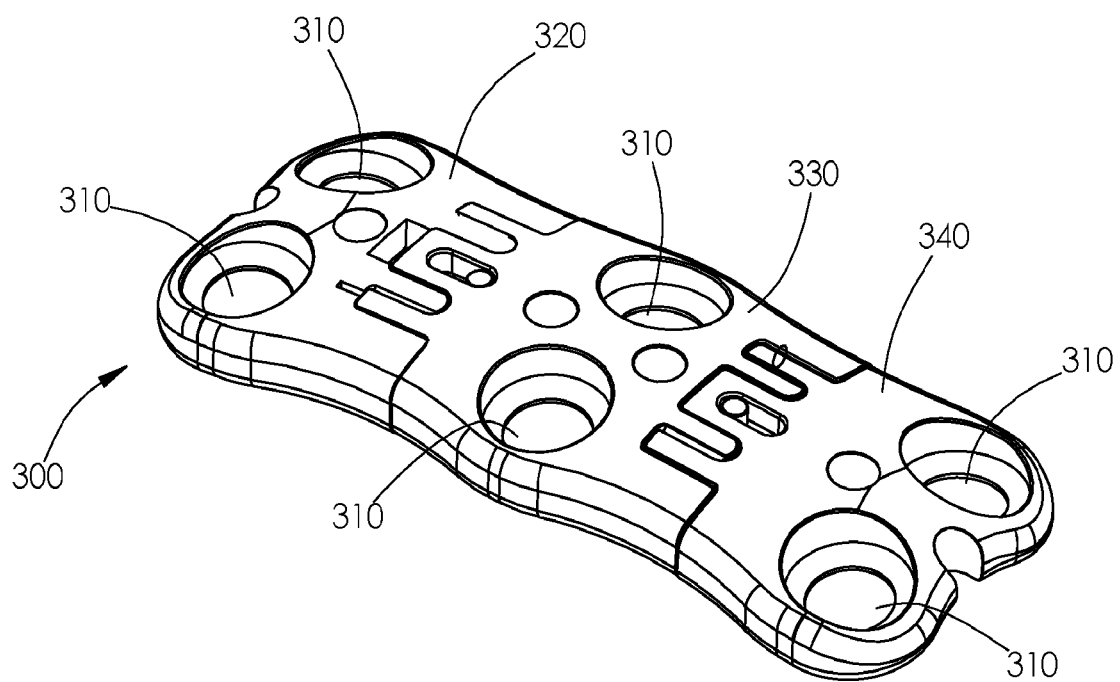
FIG. 8 is a perspective view of one example of a spinal plate for use with the fixation assembly of FIG. 1A.

The presently disclosed fixation systems can, in some embodiments, be included with any suitable spinal plate, for example, the spinal plate 300 shown in FIG. 8, to secure the spinal plate across one or more vertebrae. Generally, spinal plate 300 defines one or more apertures or openings 310 therethrough configured to receive fixation assembly 5 for securing the spinal plate 300 to vertebrae. Spinal plate 300 may have two or more sections (e.g., sections 320, 330, and 340) that are movable relative to one another. For a more detailed description of an example spinal plate, reference can be made to commonly owned U.S. Pat. No. 8,636,738, the entire disclosure of which is incorporated by reference herein.

Any of the presently disclosed embodiments, or components thereof, can be formed of any suitable material or combinations of materials such as mixed metallic materials like titanium alloy and cobalt-chromium.

Any of the presently disclosed embodiments, or components thereof can be formed using any suitable technique such as welding, fastening, machining, molding, etc. In some embodiments, one or more of the components can be secured together using any suitable technique such as welding, fastening, machining, molding, etc. Any of the components may be press-fit together.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical fixation assembly, comprising:
   a shank having an outer surface, the outer surface of the shank including a threaded portion;
   a first washer supported on the shank defining a first central axis between a first end and a second end, the first washer having a first position and a second position deformed from the first position, wherein, in the first position, the first washer is cupped only about the first central axis;
   a second washer supported on the shank defining a second central axis between a first end and a second end, the second washer having a first position and a second position deformed from the first position, wherein, in the first position, the second washer is cupped only about the second central axis, the first central axis offset from the second central axis;
   a sleeve; and
   a nut threadably engaged with the threaded portion of the shank and positioned to slide the sleeve axially along the shank to deform the first washer and enable the first washer to penetrate osseous tissue for securing the shank to osseous tissue in the second position.

2. The surgical fixation assembly according to claim 1, the first and second washers supported axially adjacent to one another at spaced apart locations along the shank.

3. The surgical fixation assembly according to claim 2, further comprising a first flat washer positioned between the first and second washers to axially space the first and second washers apart.

4. The surgical fixation assembly according to claim 3, further comprising a second flat washer positioned adjacent the second washer.

5. The surgical fixation assembly according to claim 2, wherein the second washer is inverted and angularly displaced relative to the first washer.

6. The surgical fixation assembly according to claim 1, wherein the sleeve includes a flange that extends radially outward from the sleeve and positioned to limit an insertion depth of the shank.

7. The surgical fixation assembly according to claim 6, wherein the flange includes at least one spike that extends distally therefrom.

8. The surgical fixation assembly according to claim 6, wherein the flange has an elliptical configuration.

9. The surgical fixation assembly according to claim 1, wherein the shank includes a conical tip positioned to provide a backstop for the first washer to enable the first washer to deform under a compression force applied thereto as the sleeve slides toward the conical tip.

10. The surgical fixation assembly according to claim 1, wherein the shank defines a cross-sectional shape configured to prevent the first washer from rotating about the outer surface of the shank.

11. The surgical fixation assembly according to claim 1, wherein the first washer is configured to flatten as the sleeve moves distally along the shank.

12. The surgical fixation assembly of claim 1, wherein the shank defines a longitudinal axis, and the first central axis and the second central axis are offset from the longitudinal axis.

13. The surgical fixation assembly of claim 12, wherein, when the sleeve is slid axially along the shank, the first washer deforms along the second central axis and the second washer deforms along the first central axis.

14. A method for securing a shank to osseous tissue, the method comprising:
inserting a shank into a hole into osseous tissue;
rotating a nut about the shank to drive a sleeve supported on the shank distally;
deforming a first cupped washer supported on the shank as the sleeve slides along the shank to radially expand the first cupped washer from a first position to a second position in which the first cupped washer defines a first shorter dimension and a first longer dimension and expands into osseous tissue for securing the shank to osseous tissue; and
deforming a second cupped washer on the shank as the sleeve slides along the shank to radially expand the second cupped washer from a first position to a second position in which the second cupped washer defines a second shorter dimension and a second longer dimension and expands into osseous tissue for securing the shank to osseous tissue, the first longer dimension being oriented transverse to the second longer dimension.

15. The method of claim 14, further comprising preventing the nut from moving in a proximal direction.

16. The method of claim 14, further comprising drilling the hole.

17. The method of claim 14, wherein deforming the first cupped washer includes flattening the first cupped washer.

18. The method of claim 14, wherein deforming the first cupped washer and the second cupped washer includes flattening the first cupped washer and the second cupped washer.

19. A surgical fixation assembly, comprising:
a shank having an outer surface, the outer surface of the shank including a threaded portion;
a first cupped washer supported on the shank, the first cupped washer having a first position and a second position deformed from the first position, wherein, in the second position, the first cupped washer defines a first shorter dimension and a first longer dimension;
a second cupped washer supported on the shank, the second cupped washer having a first position and a second position deformed from the first position, wherein, in the second position, the second cupped washer defines a second shorter dimension and second longer dimension, the first longer dimension being oriented transverse to the second longer dimension;
a sleeve; and
a nut threadably engaged with the threaded portion of the shank and positioned to slide the sleeve axially along the shank to deform the first cupped washer and the second cupped washer, and enable the first cupped washer to penetrate osseous tissue for securing the shank to osseous tissue.

20. The surgical fixation assembly of claim 19, wherein, when the sleeve is slid axially along the shank, the first cupped washer and the second cupped washer deforms from the first position to the second position.

* * * * *